US008113830B2

(12) United States Patent
Gill et al.

(10) Patent No.: US 8,113,830 B2
(45) Date of Patent: Feb. 14, 2012

(54) CURING LIGHT INSTRUMENT (75) Inventors: Owen J. Gill, Southbury, CT (US);
Denis J. Lachance, New Fairfield, CT (US)

(73) Assignee: Kerr Corporation, Orange, CA (US)

( * ) Notice: Subject to any disclaimer, the term of this patent is extended or adjusted under 35 U.S.C. 154(b) by 821 days.

(21) Appl. No.: 11/140,098

(22) Filed: May 27, 2005

(65) Prior Publication Data
US 2006/0269897 A1    Nov. 30, 2006

(51) Int. Cl.
*A61C 3/00*    (2006.01)
(52) U.S. Cl. .......................................... 433/29
(58) Field of Classification Search ............... 433/29–31; 600/245–246, 160, 176–180; 606/2–13, 606/88–94; 362/394, 800; 315/200 A; 345/691–693, 39, 44–46, 82, 93; 607/88–97
See application file for complete search history.

(56) References Cited

U.S. PATENT DOCUMENTS

| | | |
|---|---|---|
| 3,638,013 A | 1/1972 | Keller |
| 3,712,984 A | 1/1973 | Lienhard |
| 3,733,481 A | 5/1973 | Kuyt |
| 3,868,513 A | 2/1975 | Gonser |
| 3,970,856 A | 7/1976 | Mahaffey et al. |
| RE29,421 E | 9/1977 | Scott |
| 4,048,490 A | 9/1977 | Troue |
| 4,114,274 A | 9/1978 | Jones |
| 4,114,946 A | 9/1978 | Hoffmeister et al. |
| 4,149,086 A | 4/1979 | Nath |
| 4,185,891 A | 1/1980 | Kaestner |
| 4,186,748 A | 2/1980 | Schlager |
| 4,209,907 A | 7/1980 | Tsukada et al. |
| 4,221,994 A | 9/1980 | Friedman |
| 4,229,658 A | 10/1980 | Gonser |
| 4,230,453 A | 10/1980 | Reimers |
| 4,233,649 A | 11/1980 | Scheer et al. |

(Continued)

FOREIGN PATENT DOCUMENTS

CA    2298992    9/2000
(Continued)

OTHER PUBLICATIONS

Burgess, John O, et al.; An Evaluation of Four Light-Curing Units Comparing Soft and Hard Curing; Pract. Periodont Anesthet. Dent. 11(1), 125-132, 1999.

(Continued)

*Primary Examiner* — Todd Manahan
*Assistant Examiner* — Yogesh Patel
(74) *Attorney, Agent, or Firm* — Wood, Herron & Evans, LLP (57) ABSTRACT

An instrument for curing light-curable compounds that includes at least one light-emitting element operable for emitting light in a band of wavelengths and is capable of curing a light-curable compound. A control circuit controls the operation of the light-emitting element. The control circuit is operable for providing a power signal to the light-emitting element at a steady state power level to drive the element to emit a steady state light output. The control circuit, while continuing with a power signal at the steady state power level, is further operable to provide temporary micro-pulses in the power signal to temporarily provide an increased power level to the light-emitting element above the steady state power level before returning to the steady state power level, to thereby increase the light output of the instrument while controlling heat generated thereby.

24 Claims, 2 Drawing Sheets

U.S. PATENT DOCUMENTS

| | | | |
|---|---|---|---|
| 4,280,273 | A | 7/1981 | Vincent |
| 4,298,806 | A | 11/1981 | Herold |
| 4,308,120 | A | 12/1981 | Horst et al. |
| 4,337,759 | A | 7/1982 | Popovich et al. |
| 4,385,344 | A | 5/1983 | Gonser |
| RE31,279 | E | 6/1983 | Mefferd et al. |
| 4,391,588 | A | 7/1983 | Matsui |
| 4,398,885 | A | 8/1983 | Loge et al. |
| 4,412,134 | A | 10/1983 | Herold et al. |
| 4,445,858 | A | 5/1984 | Johnson |
| 4,450,139 | A | 5/1984 | Bussiere et al. |
| 4,610,630 | A | 9/1986 | Betush |
| 4,666,406 | A | 5/1987 | Kanca, III |
| 4,673,353 | A | 6/1987 | Nevin |
| 4,716,296 | A | 12/1987 | Bussiere et al. |
| 4,729,076 | A | 3/1988 | Masami et al. |
| 4,757,381 | A | 7/1988 | Cooper et al. |
| 4,762,862 | A | 8/1988 | Akira et al. |
| 4,792,692 | A | 12/1988 | Herold et al. |
| 4,810,194 | A | 3/1989 | Snedden |
| 4,826,431 | A | 5/1989 | Fujimura et al. |
| 4,836,782 | A | 6/1989 | Gonser |
| 4,839,566 | A | 6/1989 | Herold et al. |
| 4,846,546 | A | 7/1989 | Cuda |
| 4,888,489 | A | 12/1989 | Bryan |
| 4,935,665 | A | 6/1990 | Murata |
| 4,936,808 | A | 6/1990 | Lee |
| 4,948,215 | A | 8/1990 | Friedman |
| 4,963,798 | A | 10/1990 | McDermott |
| 4,999,310 | A | 3/1991 | Kim |
| 5,003,434 | A | 3/1991 | Gonser et al. |
| 5,007,837 | A | 4/1991 | Werly |
| 5,017,140 | A | 5/1991 | Ascher |
| 5,029,957 | A | 7/1991 | Hood |
| 5,070,258 | A | 12/1991 | Izumi et al. |
| 5,115,761 | A | 5/1992 | Hood |
| 5,147,204 | A | 9/1992 | Patten et al. |
| 5,150,016 | A | 9/1992 | Sawase et al. |
| 5,161,879 | A | 11/1992 | McDermott |
| 5,162,696 | A | 11/1992 | Goodrich |
| 5,173,810 | A | 12/1992 | Yamakawa |
| RE34,196 | E | 3/1993 | Munro |
| 5,189,751 | A | 3/1993 | Giuliani et al. |
| 5,198,678 | A | 3/1993 | Oppawsky |
| 5,201,655 | A | 4/1993 | Friedman |
| 5,233,283 | A | 8/1993 | Kennedy |
| 5,242,602 | A | 9/1993 | Richardson et al. |
| 5,265,792 | A | 11/1993 | Harrah et al. |
| 5,278,629 | A | 1/1994 | Schlager et al. |
| 5,283,425 | A | 2/1994 | Imamura |
| 5,290,169 | A | 3/1994 | Friedman et al. |
| 5,302,124 | A | 4/1994 | Lansing et al. |
| 5,312,249 | A | 5/1994 | Kennedy |
| 5,316,473 | A | 5/1994 | Hare |
| 5,328,368 | A | 7/1994 | Lansing et al. |
| 5,371,826 | A | 12/1994 | Friedman |
| 5,373,114 | A | 12/1994 | Kondo et al. |
| 5,420,768 | A | 5/1995 | Kennedy |
| 5,457,611 | A | 10/1995 | Verderber |
| 5,471,129 | A | 11/1995 | Mann |
| 5,487,662 | A | 1/1996 | Kipke et al. |
| 5,521,392 | A | 5/1996 | Kennedy et al. |
| 5,530,632 | A | 6/1996 | Shikano et al. |
| 5,535,230 | A | 7/1996 | Abe |
| 5,616,141 | A | 4/1997 | Cipolla |
| 5,617,492 | A | 4/1997 | Beach et al. |
| 5,634,711 | A * | 6/1997 | Kennedy et al. .............. 362/119 |
| 5,660,461 | A | 8/1997 | Ignatius et al. |
| 5,664,042 | A | 9/1997 | Kennedy |
| 5,678,998 | A | 10/1997 | Honkura et al. |
| 5,698,866 | A | 12/1997 | Doiron et al. |
| 5,707,139 | A | 1/1998 | Haitz |
| 5,711,665 | A | 1/1998 | Adam et al. |
| 5,741,132 | A | 4/1998 | Usui et al. |
| 5,747,363 | A | 5/1998 | Wei et al. |
| 5,759,032 | A | 6/1998 | Bartel |
| 5,803,729 | A | 9/1998 | Tsimerman |
| 5,857,767 | A | 1/1999 | Hockstein |
| 5,912,470 | A | 6/1999 | Eibofner et al. |
| 5,928,220 | A | 7/1999 | Shimoji |
| 5,931,676 | A | 8/1999 | Honkura et al. |
| 5,975,895 | A * | 11/1999 | Sullivan .......................... 433/29 |
| 6,008,264 | A | 12/1999 | Ostler et al. |
| 6,033,223 | A | 3/2000 | Narusawa et al. |
| 6,045,240 | A | 4/2000 | Hochstein |
| 6,046,460 | A | 4/2000 | Mertins |
| 6,065,965 | A | 5/2000 | Rechmann |
| 6,068,474 | A | 5/2000 | Senn et al. |
| 6,077,073 | A | 6/2000 | Jacob |
| 6,079,861 | A | 6/2000 | Woodward et al. |
| 6,086,367 | A | 7/2000 | Levy |
| 6,095,812 | A | 8/2000 | Senn et al. |
| 6,099,520 | A | 8/2000 | Shimoji |
| 6,102,696 | A | 8/2000 | Osterwalder et al. |
| 6,123,545 | A | 9/2000 | Eggler et al. |
| 6,132,213 | A | 10/2000 | Knorpp et al. |
| 6,155,823 | A | 12/2000 | Nagel |
| 6,157,661 | A * | 12/2000 | Walker et al. .............. 372/38.02 |
| 6,159,005 | A | 12/2000 | Herold et al. |
| 6,161,937 | A | 12/2000 | Rosenstatter |
| 6,168,431 | B1 | 1/2001 | Narusawa et al. |
| 6,171,105 | B1 | 1/2001 | Sarmadi |
| 6,186,786 | B1 | 2/2001 | Trushkowsky |
| 6,190,020 | B1 | 2/2001 | Hartley |
| 6,193,510 | B1 | 2/2001 | Tsimerman |
| 6,200,134 | B1 * | 3/2001 | Kovac et al. .................... 433/29 |
| 6,203,325 | B1 | 3/2001 | Honkura et al. |
| 6,208,788 | B1 | 3/2001 | Nosov |
| 6,220,722 | B1 | 4/2001 | Begemann |
| 6,257,883 | B1 | 7/2001 | Voudouris |
| 6,280,187 | B1 | 8/2001 | Slone |
| 6,280,188 | B1 | 8/2001 | Ross |
| 6,282,013 | B1 | 8/2001 | Ostler et al. |
| 6,299,450 | B1 | 10/2001 | Honkura et al. |
| 6,322,358 | B1 | 11/2001 | Senn et al. |
| 6,331,111 | B1 | 12/2001 | Cao |
| 6,345,982 | B1 | 2/2002 | Meyer |
| 6,371,826 | B1 | 4/2002 | Pestonji |
| 6,379,149 | B1 | 4/2002 | Franetzki |
| 6,382,967 | B1 | 5/2002 | Rohner et al. |
| 6,384,099 | B1 | 5/2002 | Ostler et al. |
| 6,419,483 | B1 | 7/2002 | Adam et al. |
| 6,425,761 | B1 | 7/2002 | Eibofner |
| 6,439,888 | B1 | 8/2002 | Boutoussov et al. |
| 6,465,961 | B1 | 10/2002 | Cao |
| 6,468,077 | B1 | 10/2002 | Melikechi et al. |
| 6,482,004 | B1 * | 11/2002 | Senn et al. ...................... 433/29 |
| 6,498,108 | B2 | 12/2002 | Cao |
| 6,558,829 | B1 | 5/2003 | Faris et al. |
| 6,561,806 | B2 | 5/2003 | Kyotani et al. |
| 6,634,770 | B2 | 10/2003 | Cao |
| 6,634,771 | B2 | 10/2003 | Cao |
| 6,692,251 | B1 | 2/2004 | Logan et al. |
| 6,692,252 | B2 | 2/2004 | Scott |
| 6,700,158 | B1 | 3/2004 | Cao et al. |
| 6,702,576 | B2 | 3/2004 | Fischer et al. |
| 6,709,128 | B2 | 3/2004 | Gordon |
| 6,709,270 | B2 | 3/2004 | Honkura et al. |
| 6,719,446 | B2 | 4/2004 | Cao |
| 6,719,558 | B2 | 4/2004 | Cao |
| 6,719,559 | B2 | 4/2004 | Cao |
| 6,755,647 | B2 | 6/2004 | Melikechi |
| 6,755,648 | B2 | 6/2004 | Cao |
| 6,755,649 | B2 | 6/2004 | Cao |
| 6,767,109 | B2 | 7/2004 | Plank et al. |
| 6,780,010 | B2 | 8/2004 | Cao |
| 6,783,362 | B2 | 8/2004 | Cao |
| 6,783,810 | B2 | 8/2004 | Jin et al. |
| 6,793,490 | B2 | 9/2004 | Bianchetti et al. |
| 6,799,967 | B2 | 10/2004 | Cao |
| 6,815,241 | B2 | 11/2004 | Wang |
| 6,824,294 | B2 | 11/2004 | Cao |
| 6,829,260 | B2 * | 12/2004 | Hsia et al. ........................ 372/25 |
| 6,857,873 | B2 | 2/2005 | Bianchetti |
| 6,890,175 | B2 | 5/2005 | Fischer et al. |
| 6,910,886 | B2 | 6/2005 | Cao |
| 6,918,762 | B2 | 7/2005 | Gill et al. |

| | | |
|---|---|---|
| 6,926,524 B2 | 8/2005 | Cao |
| 6,929,472 B2 | 8/2005 | Cao |
| 6,932,600 B2 | 8/2005 | Cao |
| 6,940,659 B2 | 9/2005 | McLean et al. |
| 6,953,340 B2 | 10/2005 | Cao |
| 6,954,270 B2 | 10/2005 | Ostler et al. |
| 6,955,537 B2 | 10/2005 | Cao |
| 6,957,907 B2 | 10/2005 | Fischer |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,979,193 B2 | 12/2005 | Cao |
| 6,979,194 B2 | 12/2005 | Cao |
| 6,981,867 B2 | 1/2006 | Cao |
| 6,981,876 B2 | 1/2006 | Bleckley |
| 6,986,782 B2 | 1/2006 | Chen et al. |
| 6,988,890 B2 | 1/2006 | Cao |
| 6,988,891 B2 | 1/2006 | Cao |
| 6,991,356 B2 | 1/2006 | Tsimerman |
| 6,991,456 B2 | 1/2006 | Plank |
| 6,994,546 B2 | 2/2006 | Fischer |
| 7,001,057 B2 | 2/2006 | Plank |
| 7,011,519 B2 | 3/2006 | Castellini |
| 7,029,277 B2 | 4/2006 | Gofman |
| 7,056,116 B2 | 6/2006 | Scott et al. |
| 7,066,732 B2 | 6/2006 | Cao |
| 7,066,733 B2 | 6/2006 | Logan et al. |
| 7,074,040 B2 | 7/2006 | Kanca |
| 7,077,648 B2 | 7/2006 | Cao |
| 7,086,111 B2 | 8/2006 | Hilscher et al. |
| 7,086,858 B2 | 8/2006 | Cao |
| 7,094,054 B2 | 8/2006 | Cao |
| 7,101,072 B2 | 9/2006 | Takada et al. |
| 7,106,523 B2 | 9/2006 | McLean et al. |
| 7,108,504 B2 | 9/2006 | Cao |
| 7,144,250 B2 | 12/2006 | Fischer et al. |
| 7,153,015 B2 | 12/2006 | Brukilacchio |
| 7,167,824 B2 | 1/2007 | Kallulli |
| 7,182,597 B2 | 2/2007 | Gill et al. |
| 7,189,983 B2 | 3/2007 | Aguirre et al. |
| 7,192,276 B2 | 3/2007 | Fischer et al. |
| 7,202,489 B2 | 4/2007 | Aguirre et al. |
| 7,202,490 B2 | 4/2007 | Aguirre et al. |
| 7,207,694 B1 | 4/2007 | Petrick |
| 7,210,814 B2 | 5/2007 | Scott et al. |
| 7,210,930 B2 | 5/2007 | Kovac et al. |
| 7,223,270 B2 | 5/2007 | Altshuler et al. |
| 7,224,001 B2 | 5/2007 | Cao |
| 7,252,678 B2 | 8/2007 | Ostler et al. |
| 7,267,457 B2 | 9/2007 | Ostler et al. |
| 7,271,420 B2 | 9/2007 | Cao |
| 7,273,369 B2 | 9/2007 | Rosenblood et al. |
| 7,283,230 B2 | 10/2007 | Ostler et al. |
| 7,320,593 B2 | 1/2008 | Ostler et al. |
| 7,323,849 B1 | 1/2008 | Robinett et al. |
| 7,329,887 B2 | 2/2008 | Henson et al. |
| 7,410,282 B2 | 8/2008 | Eichelberger et al. |
| 7,422,598 B2 | 9/2008 | Altshuler et al. |
| 7,485,116 B2 | 2/2009 | Cao |
| 7,530,707 B2 | 5/2009 | Plank et al. |
| 7,530,808 B2 | 5/2009 | Cao et al. |
| 7,622,467 B2 | 11/2009 | McKinnell et al. |
| 7,651,268 B2 | 1/2010 | Cao et al. |
| 7,654,086 B2 | 2/2010 | Gong et al. |
| 7,661,172 B2 | 2/2010 | Hilscher et al. |
| 7,677,888 B1 | 3/2010 | Halm |
| 7,677,890 B2 | 3/2010 | Turner |
| 7,696,728 B2 | 4/2010 | Cross et al. |
| 7,704,074 B2 | 4/2010 | Jensen |
| 7,712,468 B2 | 5/2010 | Hargadon |
| 7,728,345 B2 | 6/2010 | Cao |
| 7,733,056 B2 | 6/2010 | Hartung et al. |
| 7,758,204 B2 | 7/2010 | Klipstein et al. |
| 7,786,499 B2 | 8/2010 | Cao |
| 2001/0007739 A1 | 7/2001 | Eibofner et al. |
| 2001/0046652 A1 | 11/2001 | Ostler et al. |
| 2002/0014864 A1 | 2/2002 | Germunder et al. |
| 2002/0051367 A1 | 5/2002 | Hooker et al. |

| | | | |
|---|---|---|---|
| 2002/0115037 A1 | 8/2002 | Cao | |
| 2002/0133970 A1 | 9/2002 | Gordon et al. | |
| 2002/0168603 A1 | 11/2002 | Cao | |
| 2002/0168607 A1 | 11/2002 | Cao | |
| 2002/0175628 A1 | 11/2002 | Cao | |
| 2002/0177099 A1 | 11/2002 | Cao | |
| 2002/0180368 A1 | 12/2002 | Cao | |
| 2002/0181947 A1 | 12/2002 | Cao | |
| 2002/0190659 A1 | 12/2002 | Cao | |
| 2002/0190660 A1 | 12/2002 | Cao | |
| 2002/0197582 A1* | 12/2002 | Cao | ................ 433/29 |
| 2003/0015667 A1 | 1/2003 | MacDougald et al. | |
| 2003/0036031 A1 | 2/2003 | Lieb et al. | |
| 2003/0147258 A1 | 8/2003 | Fischer et al. | |
| 2003/0148242 A1 | 8/2003 | Fischer et al. | |
| 2003/0218880 A1 | 11/2003 | Brukilachchio | |
| 2003/0219693 A1 | 11/2003 | Cao | |
| 2004/0005524 A1 | 1/2004 | Oxman et al. | |
| 2004/0054386 A1 | 3/2004 | Martin et al. | |
| 2005/0002975 A1 | 1/2005 | Cao | |
| 2005/0077865 A1 | 4/2005 | Duban et al. | |
| 2005/0082989 A1 | 4/2005 | Jones et al. | |
| 2005/0093506 A1 | 5/2005 | Hamada et al. | |
| 2005/0096661 A1 | 5/2005 | Farrow | |
| 2005/0099824 A1 | 5/2005 | Dowling et al. | |
| 2005/0116176 A1 | 6/2005 | Acquirre | |
| 2005/0131497 A1* | 6/2005 | Suzuki | ................ 607/88 |
| 2005/0142514 A1 | 6/2005 | Scott | |
| 2005/0158687 A1 | 7/2005 | Dahm | |
| 2005/0171408 A1 | 8/2005 | Parker | |
| 2005/0196721 A1 | 9/2005 | Jackson | |
| 2006/0024638 A1 | 2/2006 | Rosenblood | |
| 2006/0252005 A1* | 11/2006 | Feinbloom et al. | ............. 433/29 |
| 2007/0128577 A1 | 6/2007 | Scott | |
| 2007/0228392 A1 | 10/2007 | Plank et al. | |
| 2008/0062703 A1 | 3/2008 | Cao | |
| 2008/0154249 A1 | 6/2008 | Cao | |
| 2008/0161783 A1 | 7/2008 | Cao | |
| 2008/0285301 A1 | 11/2008 | Wanninger | |
| 2009/0087393 A1 | 4/2009 | Jensen | |
| 2009/0092947 A1 | 4/2009 | Cao | |
| 2009/0155740 A1 | 6/2009 | Jensen | |
| 2009/0227875 A1 | 9/2009 | Cao | |
| 2009/0238779 A1 | 9/2009 | Cao | |
| 2010/0004640 A1 | 1/2010 | Cao | |
| 2010/0096643 A1 | 4/2010 | Cao | |
| 2010/0117560 A1 | 5/2010 | Cao | |
| 2010/0173267 A1 | 7/2010 | Cao | |
| 2010/0207502 A1 | 8/2010 | Cao | |

FOREIGN PATENT DOCUMENTS

| | | |
|---|---|---|
| CA | 2298993 | 9/2000 |
| DE | 19624087 | 12/1997 |
| DE | 19803755 | 8/1999 |
| EP | 000266038 | 10/1991 |
| EP | 000568666 | 11/1992 |
| EP | 000320080 | 8/1993 |
| EP | 000591613 | 4/1994 |
| EP | 000672435 | 9/1995 |
| EP | 000678282 | 10/1995 |
| EP | 000709698 | 5/1996 |
| EP | 000755662 | 7/1996 |
| EP | 000736307 | 10/1996 |
| EP | 000750889 | 1/1997 |
| EP | 000780101 | 6/1997 |
| EP | 000780103 | 6/1997 |
| EP | 000830850 | 3/1998 |
| EP | 000879582 | 11/1998 |
| EP | 000880945 | 12/1998 |
| EP | 000884025 | 12/1998 |
| EP | 000885025 | 12/1998 |
| EP | 000959803 | 12/1999 |
| EP | 000998880 | 5/2000 |
| EP | 001031326 | 8/2000 |
| EP | 001090607 | 4/2001 |
| EP | 001090608 | 4/2001 |
| EP | 001093765 | 4/2001 |
| EP | 001103232 | 5/2001 |
| EP | 001112721 | 7/2001 |

| | | |
|---|---|---|
| EP | 001138276 | 10/2001 |
| EP | 001138349 | 10/2001 |
| EP | 000830851 | 5/2002 |
| EP | 000830852 | 5/2002 |
| EP | 001206923 | 5/2002 |
| EP | 01228738 | 8/2002 |
| EP | 001253547 | 10/2002 |
| EP | 000740567 | 11/2002 |
| EP | 001374797 | 1/2004 |
| EP | 1843079 | 10/2007 |
| GB | 002212010 | 7/1989 |
| GB | 002218636 | 11/1989 |
| GB | 002329756 | 3/1999 |
| GB | 002385137 | 8/2003 |
| GR | DE2842938 | 12/1981 |
| GR | DE3411996 | 10/1985 |
| GR | DE3706852 | 8/1988 |
| GR | DE4211233 | 1/1992 |
| GR | DE9017070 | 4/1992 |
| GR | DE2951927 | 2/1997 |
| JP | 0006030275 | 2/1994 |
| JP | 07240536 | 9/1995 |
| JP | 0007240536 | 9/1995 |
| JP | 0008141001 | 6/1996 |
| JP | 08141001 | 6/1996 |
| JP | 0008194786 | 7/1996 |
| JP | 9010238 | 1/1997 |
| JP | 0009010238 | 1/1997 |
| JP | 928719 | 4/1997 |
| JP | 9187825 | 7/1997 |
| JP | 1033573 | 2/1998 |
| JP | 410033573 | 2/1998 |
| JP | 2000312688 | 11/2000 |
| JP | 2001522635 | 11/2001 |
| JP | 2003320683 | 5/2002 |
| JP | 2002200100 | 7/2002 |
| JP | 2003093405 | 4/2003 |
| JP | 2003288201 | 10/2003 |
| JP | 2004355852 | 12/2004 |
| JP | 2005212805 | 8/2005 |
| JP | 2007128667 | 5/2007 |
| JP | 2007514454 | 6/2007 |
| WO | WO8301311 | 4/1983 |
| WO | WO8404463 | 11/1984 |
| WO | WO9202275 | 2/1992 |
| WO | WO9309847 | 5/1993 |
| WO | WO9321842 | 11/1993 |
| WO | WO9507731 | 3/1995 |
| WO | WO9519810 | 7/1995 |
| WO | WO9526217 | 10/1995 |
| WO | WO9736552 | 10/1997 |
| WO | WO9737722 | 10/1997 |
| WO | WO9746279 | 12/1997 |
| WO | WO9746280 | 12/1997 |
| WO | WO9803131 | 1/1998 |
| WO | WO9803132 | 1/1998 |
| WO | WO9804317 | 2/1998 |
| WO | WO9909071 | 2/1999 |
| WO | WO9911324 | 3/1999 |
| WO | WO9916136 | 4/1999 |
| WO | WO9920346 | 4/1999 |
| WO | WO9935995 | 7/1999 |
| WO | WO0001464 | 1/2000 |
| WO | WO0002491 | 1/2000 |
| WO | WO0013608 | 3/2000 |
| WO | WO0014012 | 3/2000 |
| WO | WO0015296 | 3/2000 |
| WO | WO0041726 | 7/2000 |
| WO | WO0041767 | 7/2000 |
| WO | WO0041768 | 7/2000 |
| WO | WO0043067 | 7/2000 |
| WO | WO0043068 | 7/2000 |
| WO | WO0043069 | 7/2000 |
| WO | WO0045733 | 8/2000 |
| WO | WO0067048 | 11/2000 |
| WO | WO0067660 | 11/2000 |
| WO | WO0103770 | 1/2001 |
| WO | WO0113608 | 2/2001 |
| WO | WO0119280 | 3/2001 |
| WO | WO0124724 | 4/2001 |
| WO | WO0154770 | 8/2001 |
| WO | WO0160280 | 8/2001 |
| WO | WO0164129 | 9/2001 |
| WO | WO0168035 | 9/2001 |
| WO | WO0169691 | 9/2001 |
| WO | WO0206723 | 1/2002 |
| WO | WO0209610 | 2/2002 |
| WO | WO0211640 | 2/2002 |
| WO | WO0232505 | 4/2002 |
| WO | WO0233312 | 4/2002 |
| WO | WO0249721 | 6/2002 |
| WO | WO0256787 | 7/2002 |
| WO | WO0269839 | 9/2002 |
| WO | WO0280808 | 10/2002 |
| WO | WO2006014363 | 2/2006 |
| WO | WO2009134885 | 11/2009 |

OTHER PUBLICATIONS

Davidson-Kaban, Saliha S., et al.; The Effect of Curing Light Variations on Bulk Curing and Wall-to-Wall Quality of Two Types and Various Shades of Resin Composites; Dent. Mater. 13: 344-352, Nov. 1997.

Feltzer, A.J., et al.; Influence of Light Intensity on Polymerization Shrinkage and Integrity of Restoration-Cavity Interface; Eur. J. Oral Sciences, 103: 322-325, 1995.

Kanca, III, John and Suh, Byoung I.; Pulse Activation: Reducing Resin-Based Composite Contraction Stresses at the Enamel Cavosurface Margins; Am. J. of Dentistry, 12(3), 107-112, 1999.

Kato, Hiromasa; Relationship Between the Velocity of Polymerization and Adaptation to Dentin Cavity Wall of Light-Cured Composite; Dental Materials J. 6(1): 32-37, 1987.

Koran, Peter and Kurschner, Ralf; Effect of Sequential versus Continuous Irradiation of a Light-Cured Resin Composite on Shrinkage, Viscosity, Adhesion, and Degree of Polymerization; Am. J. of Dentistry, 11, No. 1, 17-22, 1998.

LumiLeds Lighting LLC; Luxeon™ Power Light Sources of the Future; Jan. 2001—Mike Holt.

Lumileds Lighting LLC; Application Note 1149-5, Secondary Optics Design Considerations for Super Flux LED's; Copyright © 2000 LumiLeds Lighting, Obsoletes Publication No. 5968-1215E, Publication No. AN06 (3/00).

Lumileds Lighting LLC; LED Application Note Dental Light Curing; LumiLeds Lighting Publication No. XXX(03.01), Copyright © 2000.

Lumileds Lighting LLC; Concept Evaluation Data Luxeon™ Star 5-Watt; Luxeon™ 5-Watt Preliminary Target Data Sheet, Publication No. JP10 (Jan 2002).

Lumileds Lighting LLC; Application Bulletin AB XXX; Luxeon™ Data Sheet, Publication No. xxxx-xxxx.

Lumileds Lighting LLC; Lumen Maintenance of White Luxeon™ Power Light Sources; Application Brief AB07, LumiLeds Lighting, US LLC.

Luxeon Dental Technical Data; Power Light Source; Apr. 2002.

Mayes, Joe H.; Curing Lights: An Overview; Unknown, p. 15-17.

Mehl, et al.; Softstartpolymerisation von Kompositen in Klasse-V-Kavitatent; Dtsch Zhnarzl Z. 52/1997, pp. 824-827 (in German).

Mehl, et al., Soft Start Polymerization of Composites in Class V Cavities; Dtsch Zhnarzl Z. 52/1997, pp. 824-827 (English version of #15 above.).

Mehl, A., et al., Physical Properties and Gap Formation of Light-Cured Composites With and Without 'Softstart-Polymerization'; J. of Dentistry, 25, 321-330, 1997.

Mehl, et al.; 496 The Influence of Pre-Curing on the Material Properties of Composite Resins; Journal of Dental Research, vol. 74, 1995, Special Issues S.462 (abstract).

Mills, Robin W., et al.; Blue LED's for Curing Polymer-Based Dental Filling Materials; LEO's Newsletter, Jun. 1998.

Mills, R.W., et al.; Optical Power Outputs, Spectra and Dental Composite Depths of Cure, Obtained with Blue Light Emitting Diode (LED and Halogen Light Curing Units LCU's); Oct. 26, 2002.

Reinhardt, et al.; Unischerheiten bei der Prufung von Photopolymerisation; Dtsch zahnarzl Z. 36,635-640, 1981 (in German).

Reinhardt, et al.; Uncertaintaies in the Testing of Photopolymers; Dtsch zahnarzl Z. 36, 635-640 1981.

Sakaguchi, Ronald L. and Berge, Hong Xu; Reduced Light Energy Density Decreases Post-Gel Contraction While Maintaining Degree of Conversion in Composites; J. of Dentistry, 26, 695-700, 1998.

Schlager, Kenneth J., Ignatius, Ronald W.; An LED-Array Light Source for Medical Therapy; SPIE vol. 1892 Medical Lasers and Systems II (1993) p. 26-35.

Swift, Jr., Edward J., et al. Ed.; Contemporary Photocuring Issues, Part II; J. Esthetic Dentistry, 12 (1), 50-57, 2000.

Tarle, Z., et al.; The Effect of the Photopolymerization Method on the Quality of Composite Resin Samples; J. or Oral Rehab. 25: 436-442, 1998.

TIR Technologies, Inc,; Miniaturized TIR lenses for Light Emitting Diodes; TIR Technical Publications, pp. 1-14.

Uno, Shigeru and Asmussen, Erik; Marginal Adapation of a Restorative Resin Polymerized at Reduced Rate; Scand J. Dent. Res. 1991; 99: 440-4.

Two-page International Search Report for EP07020186 mailed Jan. 7, 2009.

* cited by examiner

CURING LIGHT INSTRUMENT

FIELD OF THE INVENTION

The present invention relates to light-generating instruments for curing light-curable compounds, such as those utilized in dental applications. More particularly, the present invention relates to energy efficient curing light instruments.

BACKGROUND OF THE INVENTION

Light-curable compounds, such as adhesives and bonding or filling compounds, are widely used to attach objects to surfaces or to fill gaps or other openings. Such compounds have a particular use in dentistry, such as to bond dental work or fill gaps, such as a cavity, in a tooth. Such curable compounds are generally available in a semi-solid state, and are manipulated and positioned on a work surface or in the gap as desired, and hardened or cured into a more solid state for permanency. Curing or hardening is generally a chemical polymerization process that is promoted and driven by various curing conditions and factors. For example, a semi-solid compound or component thereof, may be cured by exposure to air or to energy, such as heat or light energy.

Today, many adhesive and filling compounds are cured by exposure to light energy, particularly visible light energy. The light curing process involves directing a beam of light, at a specific wavelength or band of wavelengths, onto a semi-solid light-curable compound to cure the compound. The compound includes light sensitive, chemical components therein which, when exposed to the light at the specific wavelength, generally polymerize to harden the compound onto the work surface to bond, fill, or coat the surface.

As noted, such light-curable compounds are widely used in dental procedures. Dentists use light-curable compounds for tooth repairs in a variety of applications including a base, a liner, a coating, a surface seal, a filling for caries and cavities, and to secure crowns or similar dental structures to a tooth surface. Generally, visible light in a somewhat narrow wavelength band, such as the blue range of the light spectrum, will be sufficient to cure most commonly used dental compounds. Once cured, the dental compound functions, for example, to reduce further tooth decay, to bond dental structures, and/or to provide additional structural support to a tooth.

Generally, curing is effected by various instruments or devices capable of generating visible light, particularly a beam of blue light, and directing this light onto a tooth surface containing the light-curable compound. The blue light penetrates into the compound layer on the tooth surface for complete curing. The duration of the exposure to blue light for proper curing of the compound layer depends upon the light-curable compound itself, thickness of the compound layer, and the power and characteristics of the blue light emitted from the curing light instrument. For example, curing a compound to provide a thin tooth surface coating or veneer will require less light energy and a shorter curing time, while curing a compound to provide a thicker, deeper filling for gaps, such as caries and cavities, will require a greater amount of light energy and a longer curing time.

Presently, various prior art dental curing light devices utilized to deliver blue light to the tooth have exhibited various drawbacks. For example, the light directed towards the tooth inevitably exposes the surrounding oral tissue to certain wavelengths of light known to be undesirable for human tissue. Hence, curing light devices must be tuned to emit light at the proper wavelength to cure a specific wavelength sensitive light-curable compound for proper curing and have their output radiation limited to within a suitable wavelength band.

In one popular prior art curing light, a light bulb emitting a large wavelength band must be filtered to yield the desired narrow band of light. For example, a halogen bulb is used as a source of light intensity, raw visible light. Filtering of unwanted wavelengths of the visible light is accomplished by use of complex filtering devices or special filters, which receive broad spectrum light from the lamp element, and allow only the light at the desired blue wavelength to pass through or reflect onto the light-curable compound. The undesired wavelengths are then deflected back into the housing of the instrument. In addition to the high heat of the halogen bulb, such filtering also adds to the accumulation of heat during operation of the instrument. The heat must be dissipated for proper device operation and therefore, large heat sinks, fans and other devices are necessary to remove or re-direct the generated heat. Furthermore, the heat degrades the operation of the bulb and shortens its effective life.

Attempts in the art have been made to address such drawbacks of bulb-based curing lights, and several products exist which utilize solid-state light-emitting devices, such as LEDs, to generate narrow spectrum blue light that is suitable for curing light-curable compounds. Such devices do not require filters and operate generally cooler than a halogen bulb. They still are subject to heat considerations. For example, when used for longer curing times, they may tend to overheat. However, if the power to the LED chip or chips is increased to provide higher output and thus reduce the curing time, there is a greater concern about damage to the LED chip.

For example, the greater the light output of an LED component or chip, the higher its internal temperature. The manufacturer of LED-based curing lights must therefore address the internal heat generation of the LED element. If the internal heat is not controlled, it will cause irreversible damage to the LED element and its internal layers and electrical connections within, thus resulting in a permanently nonfunctioning curing device. Generally, LED chip manufacturers provide recommended power limits to minimize internal heat production. However, to provide even higher output levels for reduced curing times, curing light manufacturers may be required to "drive" the LED elements beyond the recommended levels. This further increases the possibility of a "meltdown" unless very technical, costly and efficient methods are utilized in the curing device.

Thus there is currently a tradeoff in trying to reduce cure times and boost light output while managing the heat generation aspects of an LED light engine. As noted above, larger, more complicated heat dissipation systems are not desirable, and particularly may not be appropriate for an LED curing device as such devices tend to be smaller and more compact anyway, as compared to a bulb-based curing device.

An additional concern with internal element heat generation and higher light output, dental tissue temperature is also a concern. Therefore, curing light devices must provide maximal composite conversion in less time while minimizing the potential for increasing tooth temperature and its possible iatrogenic consequences.

Thus, various curing light instruments of the prior art, with or without bulbs and filtering devices, are inefficient by virtue of the emitted light available to cure the compound and their heat dissipation. As a result, these instruments require more power output from the light source, increased light emission, and/or longer curing times. Consequently, such instruments also require larger and more efficient heat dissipation components that increase their overall cost and size.

Thus, there is a need to provide a curing light instrument to cure compounds in a fast, efficient, and effective manner, while improving convenience and reducing size and overall costs.

Accordingly, it is further desirable to provide a curing light instrument which efficiently and effectively cures light-curable compounds in reduced time by maximizing the amount of light directed onto the light-curable compound while controlling the amount of heat that is internally generated in the light engine and must be dissipated.

It is also desirable to provide such curing while reducing tissue temperature at the tooth.

It is also desirable to provide a curing light instrument that is small, portable and convenient to use for curing light-curable compounds.

It is further desirable to provide a curing light instrument requiring low maintenance and radiating light from energy efficient light emitting elements having a long life.

These and other objectives are met by the present invention.

SUMMARY OF THE INVENTION

The present invention provides an instrument for curing light-curable compounds. The instrument includes at least one light-emitting element operable for emitting light in a band of wavelengths capable of curing a light-curable compound. In one embodiment, an array of such light-emitting elements is utilized to emit light in a blue wavelength in a range around 470 nm. A control circuit controls the operation of a light-emitting element, such as by controlling the power supply, which drives the light-emitting element. The control circuit is operable for providing a power signal to the light-emitting element at a steady state power level to drive the element or elements to a mid steady state light output. The control circuit is further operable, while continuing to provide the power signal at the steady state power level, to provide temporary micro-pulses above the steady state power level, to temporarily provide an increased power level to the light-emitting element. The instrument cycles between the steady state power level and the micro-pulse level to thereby increase the light output of the instrument while controlling heat generation.

DETAILED DESCRIPTION OF EMBODIMENTS OF THE INVENTION

Figure 1:
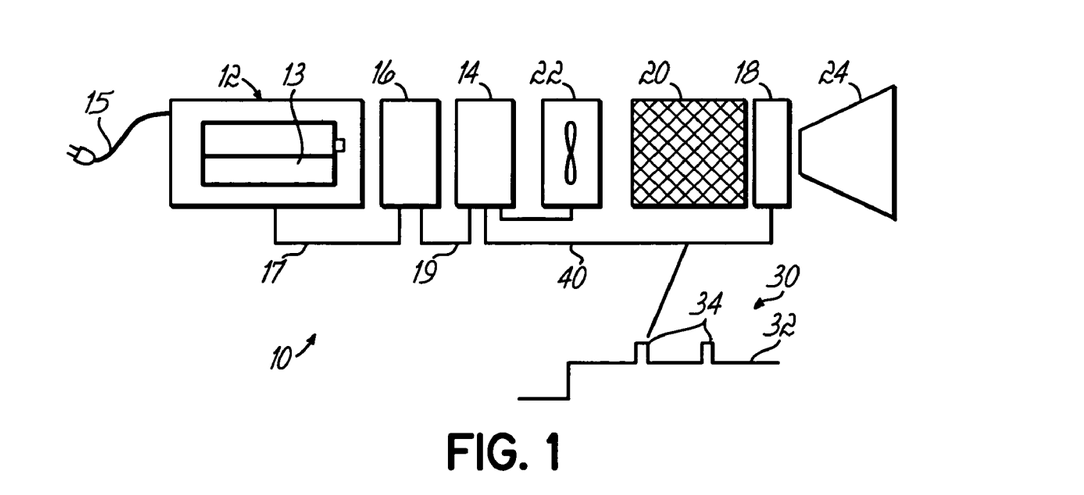
FIG. 1 is a schematic view of a curing instrument in accordance with the principles of the present invention.

The present invention is directed to an instrument for curing light-curable compounds that utilize light-emitting elements, such as solid state, light-emitting elements utilizing semiconductor junctions (e.g., LED) for emitting light in a band of wavelength capable of curing a light-curable compound. For example, the band of wavelengths might include suitable blue light in a band around 470 nm as usual for curing compounds, such as typical dental compounds. However, the invention is not limited to such a band or wavelength range. A control circuit controls the operation of the light-emitting element, or in another embodiment, an array of light-emitting elements. A control circuit is operable for providing a power signal to the light-emitting element at an initial steady state power level to drive the element to emit a steady state light output. Additionally, the control circuit, while continuing with the power signal at the steady state power level, is further operable to provide periodic micro-pulses in the power signal to periodically provide an increased power level to the light-emitting element that is above the steady state power level. In between the micro-pulses, the power signal returns to the steady state power level. In that way, the light output from the light-emitting element, or other light engine, is increased, while the heat that is generated by such a light-emitting element is controlled. In the present invention the control circuit and power signal control scheme may be utilized with any suitable instrument for curing light curable compounds. It provides the desired increased light output while controlling the heat generated by the elements, and particularly the internal heat of the layers and components of the element, such as an LED. FIG. 1 illustrates a schematic view of one such possible curing instrument, but is not meant to be limiting with respect to the curing instruments that may incorporate and be improved by the present invention.

Specifically referring to FIG. 1, an instrument for curing light-curable compounds 10 is illustrated. Such an instrument may include a power source 12, such as a battery 13 or suitable circuitry 15 for coupling to an AC outlet to provide power. The power source 12 is coupled to a power supply 14, which supplies each of the electric components of the instrument 10 with necessary power. In accordance with one aspect of the invention, a control circuit 16 is coupled between the power source 12 and power supply 14 for controlling the power supply and ultimately controlling the other electrical components of the instrument 10, and particularly the one or more light-emitting elements, of light engine 18. FIG. 1 illustrates the power source 12 coupled to control circuit 16 via connection 17, and the control circuit coupled to power supply 14 via connection 19, but other connections are suitable as well. The light engine may be coupled to a suitable heat sink 20 or other heat-dissipating element. The heat sink may take any suitable form, such as a shaped aluminum block, a heat pipe, or other suitable heat dissipation elements to draw or conduct heat away from the light engine 18 so that it may be dissipated, such as by convection. To that end, an optional fan element 22 might be utilized to facilitate greater heat dissipation. Fan 22 may be appropriately coupled to the power supply 14.

Light engine 18 may be any suitable light engine for generating or emitting light, such as in a band of wavelengths capable of curing a light-curable compound. For example, light engine 18 may be operable to generate light in the range of 438 nm 485 nm, which is a blue light range, suitable for curing many dental compounds. The light engine, in one particular embodiment of the invention, includes at least one light-emitting element such as a solid-state LED. In another embodiment, an array of a plurality of light-emitting elements is utilized to emit light from the light engine.

In one specific embodiment of the invention, the light engine includes a plurality of solid-state light-emitting elements that comprise semiconductor junctions capable of generating light within a particular band of wavelengths. Such elements are sometimes commonly referred to as LEDs. For example, the light-emitting elements might be light-emitting diodes (LEDs) or other suitable solid-state, semiconductor elements that emit light when activated or turned ON. As noted, it is preferable that the light-emitting elements emit light having wavelengths within a narrow band of wavelengths for the purposes of curing a light-curable compound, such as a dental compound. Some examples of suitable light engines and suitable curing instruments, in accordance with the principles of the present invention, are shown in co-assigned U.S. Pat. Nos. 6,200,134 and 6,692,251; and U.S. patent application Ser. No. 10/215,210, entitled "Curing Light Instrument," and filed on Aug. 8, 2002; the patents and application being incorporated herein by reference in their entireties. However, such instruments as those references show are not meant to be limiting with respect to the incorporation and use of the present invention.

Instrument 10 might also utilize a suitable optical element 24, such as a reflector, light guide, lens, protective cover, or other element for focusing, guiding, or otherwise manipulating the light generated by light engine 18, or for protecting the light-emitting elements of the light engine.

Figure 2:
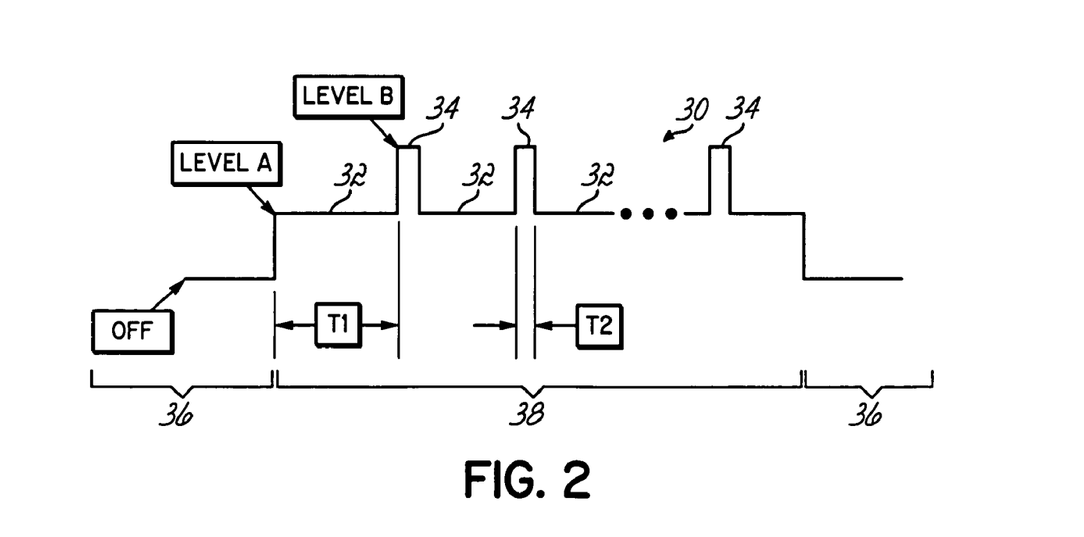
FIG. 2 is a graphical diagram of the power signal provided by the control circuit of the curing instrument in one embodiment of the invention.

Referring again to FIG. 1 and also FIG. 2, the power signal 30 provided to the light engine is shown, which includes a steady state power level 32 and a series of micro-pulses 34 providing an increased power level above the steady state power level 32. Such a power signal is provided by control circuit 16, and particularly is provided by the control circuit via control of power supply 14 or the device that generates the actual power signal 30. FIG. 2 illustrates a more detailed implementation of the power signal 30 provided by the invention.

Control circuit 16 provides an OFF state for instrument 10 when the light engine 18 is not powered, as indicated by reference numeral 36. Control circuit 16 also provides an ON state through suitable control of the power supply 14 for driving the light engine 18 to emit light for curing the light-curable compound, indicated by reference numeral 38. In the ON state, the control circuit 16 is operable for providing a power signal to the light-emitting element at a steady state power level 32, also indicated as level A in FIG. 2. More specifically, the control circuit controls power supply 14 to generate a power signal for the light engine 18 through a suitable electrical connection or coupling 40, as shown in FIG. 1. In FIG. 1, the control circuit is shown as a separate circuit electrically coupled between the power source 12 and the power supply 14. Other suitable electrical connections and couplings may be utilized. For example, the control circuit may be part of the actual power supply to control the power signal 30 that is output on connection or line 40.

The power signal at the steady state power level 32 may be at any suitable level for providing a suitable light output emitted from the light-emitting elements to cure a compound. The power signal may be either in the form of a current or voltage, which is applied either to light-emitting elements or an array of light-emitting elements, such as an LED array. In one embodiment, a steady state power level might be a 1.0 Amp drive current. Simultaneous with the steady state power level, or while continuing to supply a power signal at the steady state power level, the control circuit 16 is further operable to provide, or rather to have the power supply 14 generate, periodic micro-pulses 34 in the power signal to periodically provide an increased power level to the light-emitting element and thus increase the light output. The micro-pulses provide a power level above the steady state power level 32. Such level is indicated as level B in FIG. 2. Each micro-pulse has a duration T2 in relation to the duration of the preceding steady state power level T1 as shown in FIG. 2. The micro-pulses and their associated power level are provided for a significantly shorter time than the steady state power level. That is, T2 is significantly smaller than T1. For example, in some embodiments, the micro-pulses may occur approximately every 0.5 to 2.0 seconds during the provision of the steady state power level. The intervals between the micro-pulses may also depend on the duration of the micro-pulse. For example shorter micro-pulses may allow them to be generated more frequently without causing heat generation concerns. Other micro-pulse intervals might also be used in addition to the range set forth above. But generally, the micro-pulses are short compared to the intervening time at the steady state level. In that way, the light output from the light engine 18 is increased briefly to provide a greater power level, thus reducing the curing time while still controlling the heat generated internally in the elements of the light engine. For example, constantly driving the light engine, such as an LED array, at the higher level B, generates undesirable heat characteristics, and causing overheating and possibly failure of the array and the array elements. The present invention addresses such a drawback by providing an increase in the light output of the instrument while controlling the heat generated in the light-emitting elements.

In one embodiment of the invention, the micro-pulses occur approximately every 0.75 seconds (T1=0.75 seconds) and last approximately 0.25 seconds (T2=0.25 seconds). That is, a micro-pulse occurs and is completed approximately every second (T1+T2=1 second). That is, the micro-pulse lasts 0.25 seconds for each 1 second of exposure of the light-curable compound. Of course, the micro-pulses may be of shorter or longer duration. In some embodiments, the micro-pulses may have a duration of approximately 0.1 to 0.5 seconds. Of course, other durations may also be utilized based upon the operation of the invention.

In accordance with another aspect of the present invention, the increased power level of the micro-pulses, whether a current or voltage signal may be approximately 30 to 50 percent above the steady state power level. For example, level B will exceed level A by a percentage in that range. In one embodiment of the invention, the increased power level of the micro-pulse might be 1.5 Amps and, thus, exceed the steady state power level of 1.0 Amp by approximately 50 percent.

The cure time as indicated by reference numeral 38 in FIG. 2 may be any desirable time suitable for providing an adequate cure. In one embodiment, the instrument 10 might have selectable cure cycles of 5 seconds, 10 seconds, etc. In the example noted wherein T1=0.75 seconds and T2=0.25 seconds, there is generally a micro-pulse about every one second of cure time. Therefore, for a five second cure time or cycle, there may be approximately five micro-pulses. For a ten second cure time, there may be approximately ten micro-pulses, and so on. The invention may provide a steady state power level and micro-pulses for a cure time in a range of 1 to 30 seconds, or longer or shorter as needed for proper curing of the light-curable compound or the particular application of such a compound.

In one important aspect of the present invention, at least steady state power is provided to the light engine at all times to provide a consistent and sufficient light output from light engine 18 to provide a proper cure. That is, at the end of each micro-pulse duration, the power signal returns to the steady state power level. The micro-pulses by increasing the effective light output power of the instrument significantly reduce the cure time that might be necessary if the power signal is simply maintained at the steady state power level. The micro-pulse signal above a steady state level provided by the invention might also be called periodic level shifting. For example, utilizing the present invention, a cure application that may take 7-10 seconds with just a steady input signal, now can be reduced to a 5 second cure utilizing the combination of providing micro-pulses simultaneously with, but above, a steady state power level in accordance with the invention. For example, utilizing a suitable light engine, such as a Luxeon V available from Lumileds Lighting, LLC of San Jose, Calif., the light output may jump from a steady state light output level of 1200 mW/cm$^2$ to approximately 1600 mW/cm$^2$. Of course, other light outputs might be achieved depending upon the light engine and the number of elements utilized in the light engine. For example, a light output may be provided by the invention in the range of 600 mW/cm$^2$ to 2500 mW/cm$^2$.

Figure 3:
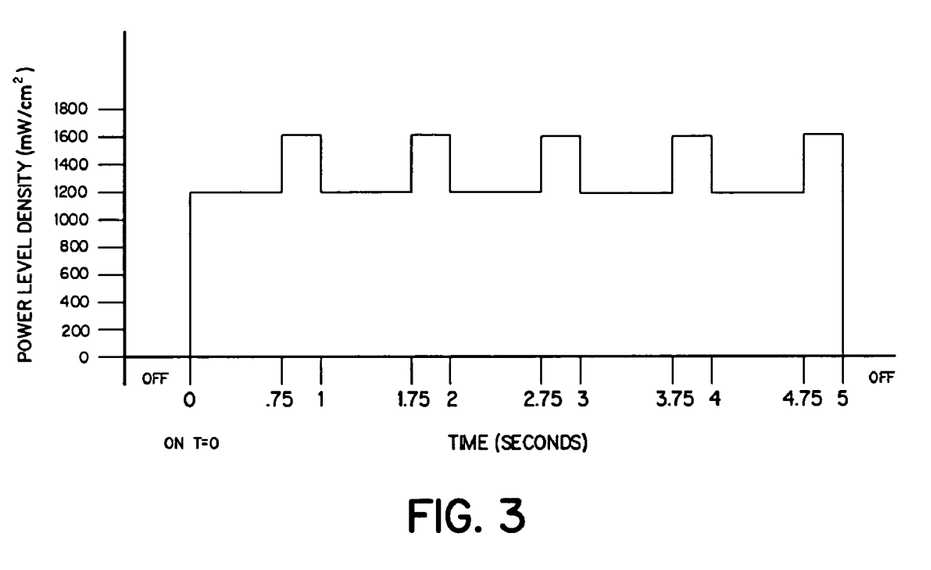
FIG. 3 is a further graphical diagram of the light output over time with the invention.

Referring to FIG. 3, a graph shows the output power density of a light engine for a five second cure time utilizing the present invention involving micro-pulses from a steady state power level. As shown in the Y-axis, the power density may be increased from a steady state level of around 1200 mW/cm$^2$ to around 1600 mW/cm$^2$. In accordance with the invention, however, although the light output is significantly increased and, thus, the curing time is decreased, the internal heat generated by the light-emitting elements is controlled to prevent overheating and failure of the light engine. The present invention provides increased LED output without raising internal chip or circuit temperatures of the light-emitting elements to critical failure levels. In that way, a higher power and more effective LED light output may be provided without fear of causing irreparable damage to the light-emitting elements. At no time during the exposure do the power levels drop to 0, as is common with devices that use modulated power sources. Rather, very high levels of power density (baseline increased by micro-pulses), are seen wherein the light-emitting elements may be driven to achieve maximum output values slightly beyond in a pulse fashion.

An additional benefit of the invention is lowered intrapulpal temperature levels, thus maintaining the heat levels produced in tissue around a cure site in a more desirable range. Furthermore, the present invention provides an ability to efficiently drive light-emitting elements, such as LEDs, without requiring higher power LED technology, such as in the form of individual LEDS, which generate a higher light output. In accordance with one aspect of the present invention, the micro-pulses above a steady state power level may increase the light output of the curing instrument to a level approximately 30 percent above the steady state light output to thus achieve the desirable outcomes as noted above, while preventing instrument overheating and failure.

While the above-discussed embodiments of the invention utilize repeated micro-pulses of approximately equal duration that are separated by generally the same duration between micro-pulses, another embodiment of the invention might utilize micro-pulses wherein successive micro-pulses are of different durations, or are separated by different durations at the steady state level, or both. For example, there may be a duration of anywhere in the range of from approximately 0.5 to 2.0 seconds at the steady state power level between successive micro-pulses and that duration may vary from one successive micro-pulse to the next. The successive micro-pulses may also have a duration of anywhere in the range from approximately 0.1 to 0.5 seconds each, for example, and may differ from one successive pulse to the next.

While the present invention has been illustrated by a description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details and representative apparatus and method, and illustrative examples shown and described. Accordingly, departures may be made from such details without departing from the spirit or scope of the applicant's general inventive concept.

What is claimed is:

1. An instrument for curing light-curable compounds comprising:
    at least one solid-state light-emitting element operable for emitting light in a band of wavelengths capable of curing a light-curable compound;
    a control circuit for controlling the operation of the at least one light-emitting element, the control circuit, in an ON state, operable for providing a power signal to the light-emitting element generally immediately at a generally constant steady state power level to drive the element to emit a steady state light output;
    the control circuit, while continuing with a power signal at the steady state power level, further operable to provide temporary micro-pulses in the power signal to temporarily provide an increased power level to the at least one light-emitting element above the steady state power level before returning to the steady state power level;
    the time duration of the micro-pulses and the resulting increased power level of the power signal above the steady state power level being less than the time duration of the power signal at the steady state power level to thereby increase the light output of the instrument while controlling heat generated by the at least one light-emitting element.

2. The instrument of claim 1 wherein the micro-pulses are provided periodically during the steady state power level.

3. The instrument of claim 2 wherein the micro-pulses occur approximately every 0.5 to 2.0 seconds during the duration of the power signal at the steady state power level.

4. The instrument of claim 2 wherein the micro-pulses occur approximately every second during the duration of the power signal at the steady state power level.

5. The instrument of claim 1 wherein the micro-pulses have a duration of approximately 0.1 to 0.5 seconds.

6. The instrument of claim 1 wherein the micro-pulses have a duration of approximately 0.25 seconds.

7. The instrument of claim 1 wherein the micro-pulses provide an increased power level of the power signal that is approximately 30 percent to 50 percent above the steady state power level.

8. The instrument of claim 1 further comprising an array of a plurality of solid state light-emitting elements.

9. The instrument of claim 1 wherein the control circuit provides the steady state power level and micro-pulses for a cure time in the range of 1 to 30 seconds.

10. The instrument of claim 1 wherein the control circuit provides the power signal by controlling a power supply that generates the power signal.

11. The instrument of claim 1 wherein the light output provided is in the range of 600 mW/cm$^2$ to 2500 mW/cm$^2$.

12. The instrument of claim 1, wherein the micro-pulses increase the light output to a level approximately 25 percent to 50 percent above the steady state power level.

13. The instrument of claim 1 wherein the micro-pulses occur in the power signal in the range of approximately every 0.5 to 2.0 seconds during provision of the power signal at the steady state power level.

14. An instrument for curing light-curable compounds comprising:
    at least one solid state light-emitting element operable for emitting light in a band of wavelengths capable of curing a light-curable compound;
    a control circuit for controlling the operation of the at least one light-emitting element, the control circuit operable for providing a signal at a generally constant steady state power level to the light-emitting element to drive the element to emit a steady state light output and simultaneously providing temporary micro-pulses in the power signal to provide an increased power level above the steady state power level;

the time duration of the micro-pulses and the resulting increased power level of the power signal above the steady state power level being less than the time duration of the power signal at the steady state power level to thereby increase the light output of the instrument while controlling heat generated by the at least one light element.

15. The instrument of claim 14 wherein the micro-pulses are provided periodically during the steady state power level.

16. The instrument of claim 15 wherein the micro-pulses occur approximately every 0.5 to 2.0 seconds during the duration of the power signal at the steady state power level.

17. The instrument of claim 14 wherein the micro-pulses have a duration of approximately 0.1 to 0.5 seconds.

18. The instrument of claim 14 wherein the micro-pulses provide an increased power level that is approximately 30 to 50 percent above the steady state power level.

19. The instrument of claim 14 further comprising an array of a plurality of solid state light-emitting elements.

20. The instrument of claim 14 wherein the control circuit provides the steady state power level and micro-pulses for a cure time in the range of 1 to 30 seconds.

21. The instrument of claim 14 wherein the control circuit provides the power signal by controlling a power supply that generates the power signal.

22. The instrument of claim 14 wherein the light output provided is in the range of 600 mW/cm$^2$ to 2500 mW/cm$^2$.

23. The instrument of claim 14, wherein the micro-pulses increase the light output to a level approximately 25 percent to 50 percent above the steady state power level.

24. The instrument of claim 14 wherein the micro-pulses occur in the power signal in the range of approximately every 0.5 to 2.0 seconds during provision of the power signal at the steady state power level.

\* \* \* \* \*